(12) United States Patent
Modi

(10) Patent No.: US 6,849,263 B2
(45) Date of Patent: Feb. 1, 2005

(54) PHARMACEUTICAL COMPOSITIONS FOR BUCCAL DELIVERY OF PAIN RELIEF MEDICATIONS

(75) Inventor: Pankaj Modi, Ancaster (CA)

(73) Assignee: Generex Pharmaceutical Incorporated, Toronto (CA)

( * ) Notice: Subject to any disclaimer, the term of this patent is extended or adjusted under 35 U.S.C. 154(b) by 162 days.

(21) Appl. No.: 10/222,699

(22) Filed: Aug. 16, 2002

(65) Prior Publication Data

US 2003/0035831 A1 Feb. 20, 2003

Related U.S. Application Data

(63) Continuation-in-part of application No. 09/574,504, filed on May 19, 2000, now Pat. No. 6,451,286, which is a continuation-in-part of application No. 09/519,285, filed on Mar. 6, 2000, now Pat. No. 6,375,975, which is a continuation-in-part of application No. 09/386,284, filed on Aug. 31, 1999, now Pat. No. 6,312,665, which is a continuation-in-part of application No. 09/251,464, filed on Feb. 17, 1999, now Pat. No. 6,436,367.

(60) Provisional application No. 60/113,239, filed on Dec. 21, 1998.

(51) Int. Cl.[7] .......................... A61F 13/00; A61K 38/00; A61K 9/12

(52) U.S. Cl. ........................ 424/400; 424/434; 424/450; 424/45; 424/725; 424/85.2; 514/2; 514/946

(58) Field of Search ................................. 424/400, 434, 424/450, 725, 85.2, 45, 435, 489, 422; 514/2, 946

(56) References Cited

U.S. PATENT DOCUMENTS

| | | |
|---|---|---|
| 4,156,719 A | 5/1979 | Sezaki et al. |
| 4,582,835 A | 4/1986 | Lewis et al. |
| 4,614,730 A | 9/1986 | Hansen et al. |
| 4,661,492 A | 4/1987 | Lewis et al. |
| 4,673,679 A | 6/1987 | Aungst et al. |
| 4,900,730 A | 2/1990 | Miyauchi |
| 5,004,611 A | 4/1991 | Leigh |
| 5,053,389 A | 10/1991 | Balschmidt et al. |
| 5,230,884 A | 7/1993 | Evans et al. |
| 5,240,932 A | 8/1993 | Morimoto et al. |
| 5,292,499 A | 3/1994 | Evans et al. |
| 5,306,483 A | 4/1994 | Mautone |
| 5,376,646 A | 12/1994 | Pittrof et al. |
| 5,492,688 A | 2/1996 | Byron et al. |
| 5,514,670 A | 5/1996 | Friedman et al. |
| 5,569,450 A | 10/1996 | Duan et al. |
| 5,591,713 A | 1/1997 | Igari et al. |
| 5,629,011 A | 5/1997 | Illum |
| 5,653,987 A | 8/1997 | Modi et al. |
| 5,656,277 A | 8/1997 | Berlati et al. |
| 5,665,700 A | 9/1997 | Cho et al. |
| 5,690,954 A | 11/1997 | Illum |
| 5,747,066 A | 5/1998 | Pittrof et al. |
| 5,747,445 A | 5/1998 | Backstrom et al. |
| 5,981,591 A | 11/1999 | Deihl |
| 6,017,545 A | 1/2000 | Modi |
| 6,042,811 A | 3/2000 | Duan et al. |
| 6,090,407 A | 7/2000 | Knight et al. |
| 6,110,486 A | 8/2000 | Dugger, III |
| 6,193,997 B1 | 2/2001 | Modi |
| 6,214,375 B1 | 4/2001 | Modi |
| 6,221,378 B1 | 4/2001 | Modi |
| 6,225,343 B1 | 5/2001 | Behl et al. |
| 6,231,882 B1 * | 5/2001 | Modi .................. 424/434 |
| 6,255,502 B1 | 7/2001 | Penkler et al. |
| 6,261,539 B1 | 7/2001 | Adjei et al. |
| 6,271,200 B1 | 8/2001 | Modi |
| 6,312,665 B1 | 11/2001 | Modi |
| 6,350,458 B1 * | 2/2002 | Modi .................. 424/400 |
| 6,375,975 B1 | 4/2002 | Modi |
| 6,436,367 B1 | 8/2002 | Modi |
| 6,451,286 B1 | 9/2002 | Modi |
| 6,485,706 B1 * | 11/2002 | McCoy et al. ......... 424/45 |

FOREIGN PATENT DOCUMENTS

| | | |
|---|---|---|
| EP | 0 200 383 | 12/1986 |
| EP | 0 272 097 | 6/1988 |
| WO | WO 96/40057 | 12/1996 |
| WO | WO 97/42938 | 11/1997 |
| WO | WO 99/22703 | 5/1999 |
| WO | WO 00/47203 | 8/2000 |

OTHER PUBLICATIONS

Editor Alfonso R. Gennaro, Remington's Pharmaceutical Sciences, 17 Edition, 1985, Pp 293–297 & 1662–1677, Mack Publishing Company, Easton, Pennsylvania 18042.

Dieter Kohler, Systemic Therapy with Aerosols, Aerosols in Medicine: Principles, Diagnosis and Therapy, 2nd rev. ed., Pp 303–319, 1993 Elsevier Science Publishers BV.

Vincent Hl Lee et al., Mucosal Penetration Enhancers for Facilitation of Peptide and Protein Drug Absorption, Critical Reviews in Therapeutic Drug Carrier Systems, Pp 91 139 140 8(2):91–192 (1991).

John S. Patton et al., Pulmonary Delivery of Peptides and Proteins, Advanced Drug Delivery Reviews, Pp 179–196, 8 (1992), Elsevier Science Publishers BV.

Hans Schreier et al., Pulmonary Delivery of Liposomes, Journal of Controlled Release, Pp 209–223, 24 (1993) Elsevier Science Publishers BV.

Amir H. Shojaei, Buccal Mucosa as a Route for Systemic Drug Delivery: A Review, J Pharm Pharmaceut Sci, 1 (1):1:15–30, 1998.

* cited by examiner

Primary Examiner—Gary Kunz
Assistant Examiner—Mina Haghighatian
(74) Attorney, Agent, or Firm—Eckert Seamans Cherlin & Mellott, LLC

(57) ABSTRACT

Pharmaceutical compositions comprising a narcotic analgesic in mixed micellar form are disclosed. The mixed micelles are formed from an alkali metal alkyl sulfate, and other micelle-forming compounds as described in the specification. Micelle size ranges between about 1 and 10 nanometers. Methods for making and using the compositions are also disclosed. A preferred method for administering the present composition is through the buccal mucosa of the mouth.

32 Claims, 1 Drawing Sheet

US 6,849,263 B2

PHARMACEUTICAL COMPOSITIONS FOR BUCCAL DELIVERY OF PAIN RELIEF MEDICATIONS

CROSS REFERENCE TO RELATED APPLICATIONS

This application is a continuation-in-part of U.S. application Ser. No. 09/574,504, filed May 19, 2000 now U.S. Pat. No. 6,451,286, which is a continuation-in-part of application Ser. No. 09/519,285, filed Mar. 6, 2000, now U.S. Pat. No. 6,375,975, which is a continuation-in-part of U.S. application Ser. No. 09/386,284 filed Aug. 31, 1999, now U.S. Pat. No. 6,312,665 which is a continuation-in-part of U.S. application Ser. No. 09/251,464 filed Feb. 17, 1999 now U.S. Pat. No. 6,436,367, which claims priority to provisional Application No. 60/113,239 filed Dec. 21, 1998.

FIELD OF THE INVENTION

The present invention relates to an improved pharmaceutical composition comprising a narcotic analgesic in micellar form. The narcotic analgesic compositions are particularly effective in buccal delivery, for immediate relief of pain. The present invention further relates to methods for preparing and using these compositions.

BACKGROUND INFORMATION

Patients with both chronic non-cancer (e.g., post-operative surgical pain) and cancer pain present a number of challenges to their treating physicians. One such challenge is whether to use oral opioids in their treatment plan; some patients are not good candidates due to a combination factors, including poorly defined pathology, significant psychosocial problems, manipulative behavior, dependence, and tolerance. However, opioid therapy can yield adequate relief in more than three quarters of patients with severe pain. This justifies its use as a first-line therapy for patients with moderate to severe cancer pain or post-operative surgical pain. Many patients with mild pain respond adequately to non-opioid drugs, and these should be considered first in such cases. Since the response to opioids is highly individual, sequential trials (so-called opioid rotation) may be needed to identify the drug that yields the most favorable balance between analgesia and side effects.

Although the oral route is usually preferred for chronic opioid therapy, other routes may be needed for diverse reasons, including dysphagia, impaired gastrointestinal function, and noncompliance with oral agents. Opioid delivery can be accomplished via many other approaches, including the transdermal route, continuous subcutaneous or intravenous infusion, and intraspinal infusion. However, there continues to be a need for effective methods of delivery that do not involve injection and yet accomplish the goal of immediate and lasting pain relief.

SUMMARY OF THE INVENTION

The present invention solves the above need and provides a new approach to the treatment of breakthrough pain, with a pharmaceutical composition comprising a narcotic analgesic, an alkali metal alkyl sulfate, an isotonic agent, a polyoxyethylene ether and a bile salt, in a suitable solvent. The narcotic analgesic is present in mixed micellar form, with a micelle size of approximately one to 10 nanometers (nm). The pharmaceutical formulation allows delivery of a narcotic analgesic to the mouth of a patient, through the buccal mucosa, in an aerosol spray, and provides a needle free pain therapy for administration of narcotics and pain relief drugs.

The mucosal membranes of the mouth contain a thin membrane which guards a large surface area, composed of many superficial blood vessels in direct contact with the circulation. A fast moving aerosol, however, can traverse this thin membrane. After penetration through these superficial layers, the drug molecules are rapidly absorbed, with the aid of the absorption enhancers, into the blood stream and appear in the circulation within 10 minutes of application.

Methods for making and using the present pharmaceutical compositions are also within the scope of the present invention.

It is therefore an aspect of the present invention to provide a pharmaceutical composition comprising a narcotic analgesic and a combination of micelle forming compounds.

It is a further aspect of the invention to provide such a composition wherein the narcotic analgesic is in micellar form.

It is a further aspect of the invention to provide a method for administering a narcotic analgesic, particularly to the buccal region of a patient.

These and other aspects of the invention will be apparent from the following disclosure and appended claims.

BRIEF DESCRIPTION OF THE DRAWINGS

The invention is further illustrated by the following non-limited drawings in which.

DETAILED DESCRIPTION OF THE INVENTION

Figure 1:
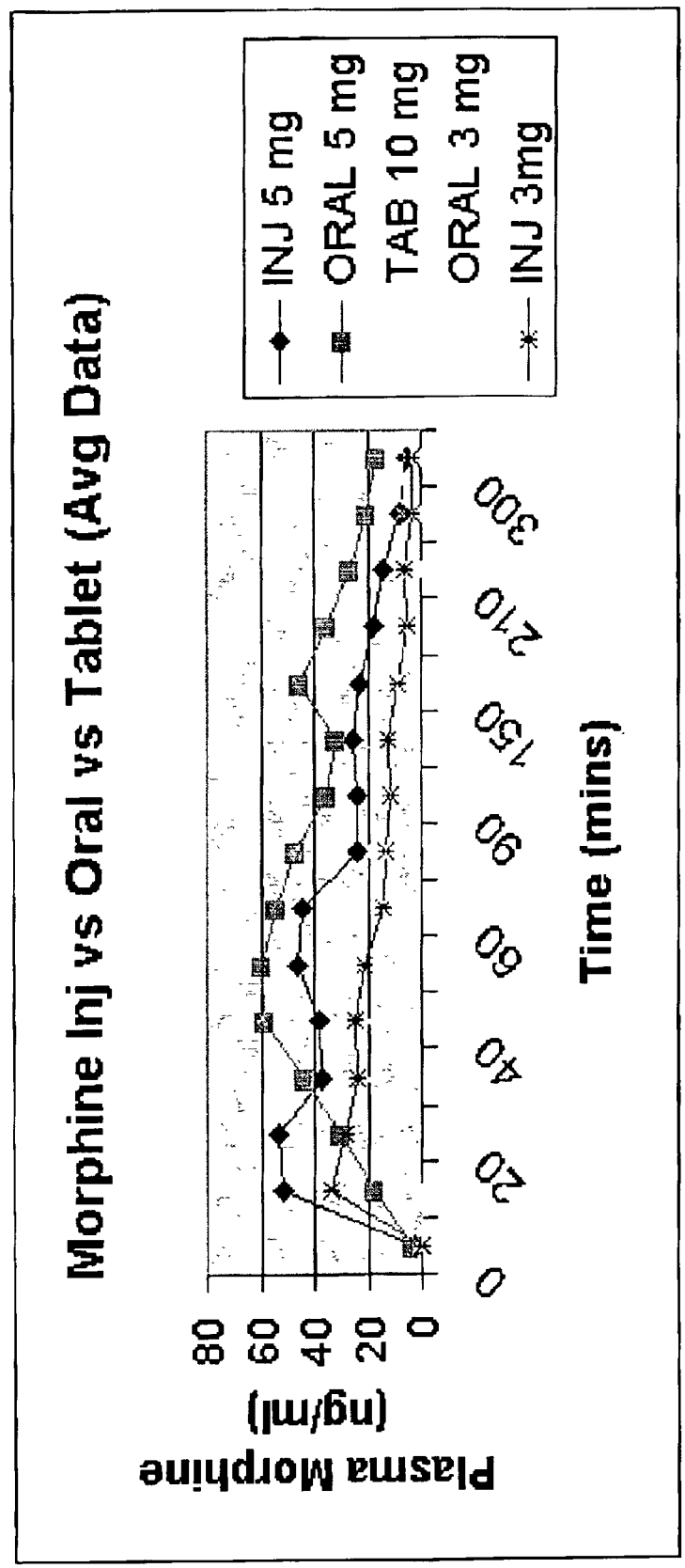
FIG. 1 displays graphically the data presented in Table 1, plasma levels measured at different time periods, when the drug is delivered via tablet, injection, and the method of the present invention (sprayed to the buccal mucosa).

The present invention is directed to a pharmaceutical composition comprising an effective amount of a narcotic analgesic, an alkali metal alkyl sulfate, and a polyoxyethylene ether (POE) in a suitable solvent. The alkali metal alkyl sulfate and polyoxyethylene ether are each present in a concentration of between about 0.1 and 30 wt./wt. % of the total composition, and the total concentration of the alkali metal alkyl sulfate and polyoxyethylene ether together is less than 50 wt./wt. % of the total composition. The narcotic analgesic is in micellar form.

Optionally, the composition further comprises a bile salt. When present, the concentration of bile salt will be between about 0.1 to 30 wt./wt. % of the total formulation. The composition may also optionally comprise an isotonic agent; when present, the concentration of the isotonic agent will be between about 0.1 to 30% of the total formulation. The concentration of alkali metal sulfate, POE, bile salt and isotonic agent together will be less than about 50% of the total formulation.

The pharmaceutical formulation is comprised of mixed micelles made from a combination of absorption enhancers. As used herein the term "mixed micelles" refers to at least two different types of micelles, each of which has been formed using different micelle forming compounds. For example, the present compositions comprise a mix of micelles formed between the pharmaceutical agent and alkali metal alkyl sulfate, and micelles formed between the pharmaceutical agent and polyoxyethylene ether or bile salt. It will be understood that each individual micelle can be formed from more than one micelle-forming compound as well. The mixed micelles of the present invention tend to be smaller than the pores of the membranes in the oral cavity. It is therefore believed that the extremely small size of the present mixed micelles helps the encapsulated active agent penetrate efficiently through the oral mucosae. Thus, the present compositions offer increased bioavailability of active drug, particularly across oral mucosae, when compared with pharmaceutical preparations known in the art.

The narcotic analgesic exists in micellar form in the present pharmaceutical compositions. As will be appreciated by those skilled in the art, a micelle is a colloidal aggregate of amphipathic molecules in which the polar hydrophilic portions of the molecule extend outwardly while the non-polar hydrophobic portions extend inwardly. Polyoxyethylene ethers, alkali metal alkyl sulfates and bile acids are micelle-forming compounds. It is believed that the presence of the micelles significantly aids in the absorption of the macromolecular pharmaceutical agent both because of their enhanced absorption ability, and also because of their size.

The mixed micelles encapsulate and protect the drug molecules from degradation. The formulation can be provided as an aerosol spray, and delivered to the mouth of a patient using a metered dose dispenser. Using a metered dose dispenser which delivers a high velocity, fine droplet aerosol, mouth deposition is dramatically increased as compared with conventional spray technology.

The particle size of the micelles will typically be in the range of 1 to 10 nanometers; many will range between 1 and 5 nanometers in size. The shape of the micelle can vary and can be, for example, prolate, oblate or spherical; spherical micelles are most typical.

As used herein, the term "narcotic analgesic" includes, but is not limited to, common opioids such as morphine, diamorphine, ethyl morphine, cocaine, dihydrocodeine, pethidine/meperidine, methadone hydromorphone, oxycodone, fentanyl, sufentanil and buprenorphine. Other narcotic analgesics are also contemplated. Preferred are morphine and fentanyl. Morphine is the standard opioid against which others are judged, in terms of immediacy of pain relief, duration, and adverse effects. As will be understood by one skilled in the art, the narcotic analgesics will typically be available in the salt form of the compound, for example morphine hydrochloride or morphine sulfate, and fentanyl citrate. Other salt forms of the active agent, such as tartrate, citrate, phosphate are also contemplated as being within the present invention. Where the salt form of morphine is used, morphine sulfate is the preferred salt.

An effective amount of the narcotic analgesic should be included in the present composition. As used herein, the term "effective amount" refers to that amount of the pharmaceutical agent needed to bring about the desired pain relief. It will be appreciated that the effective amount will vary depending on the particular agent used, the parameters determined for the agent, the nature and severity of the disorder being treated, the patient being treated, and the route of administration. The determination of what constitutes an effective amount is well within the skill of one practicing in the art. As used herein, the term "patient" refers to members of the animal kingdom, including but not limited to humans, who are under medical care.

The size of the starting dose varies with the severity of the pain, previous exposure to opioid, and the medical condition of the patient. In patients with limited opioid exposure, the starting dose by injection or intravenous infusion is equivalent to 5 to 10 mg of morphine every four hours. The appropriate dosing regimen is well within the ability of one skilled in the art to determine, as narcotic analgesics have been used for many years in the treatment of pain.

The goal is to achieve a favorable balance between analgesia and side effects through a process of gradual dose adjustment. In response to poorly controlled pain, the dose should be increased unless precluded by treatment-limiting side effects.

The maximal efficacy of a specific opioid is determined by the development of intolerable side effects during dose titration. Hence, the management of side effects is fundamental to therapy, potentially improving the balance between analgesia and toxicity and also allowing the use of more effective doses. The most common side effects include gastrointestinal disturbances (constipation, nausea, vomiting) and neuropsychological functioning.

Typically, the present formulations will contain pharmaceutical agents in a concentration between about 0.1 and 30 wt./wt. % of the total composition, more preferably between about 0.1 and 10 wt./wt. %.

Any alkali metal alkyl sulfate can be used in the present compositions, provided compatibility problems do not arise. Preferably, the alkyl is a C8 to C22 alkyl, more preferably lauryl (C12). Any alkali metal can be utilized, with sodium being preferred. The alkali metal alkyl sulfate is generally present in a concentration of between about 0.1 and 30 wt./wt. % of the total composition; a concentration of less than about 5 wt./wt. % of the total composition is preferred.

Pharmaceutically acceptable salts and analogues of any of these compounds are also within the present scope as are mixtures or combinations of any of these compounds. Preferably, each of these compounds (the alkali metal alkyl sulfate, polyoxyethylene ether and bile acid/salt) is present in a concentration of less than about 5 wt./wt. % of the total composition.

Suitable isotonic agents include, but are not limited to, saccharides such as sorbitol and mannitol, and polyhydric alcohols such as glycerin, polyglycerin, propylene glycol and the like, and dibasic sodium phosphate. Preferred is glycerin. The isotonic agent serves to keep the micelles in solution. Glycerin can function both as a micelle forming compound and an isotonic agent; when dibasic sodium phosphate is used it will also serve to inhibit bacterial growth.

As used herein, the term "bile acid" includes, but is not limited to, cholic acid derivatives such as cholic, glycocholic, chenodeoxycholic, taurocholic, glycodeoxycholic and taurodeoxycholic acids. Any bile acids, or salt thereof, can be used in compositions of the present invention. Preferred is sodium glycocholate. Because the present invention uses relatively low concentrations of bile salts, problems of toxicity associated with the use of these salts is minimized, if not avoided.

As used herein, the term "polyoxyethylene ethers" (also referred to as polyethylene glycols) includes, but is not limited to, any of several condensation polymers of ethylene glycol with the general formula $HOCH_2$ ($CH_2OCH_2$) or $CH_2OH$ or H ($OCH_2CH_2$) or OH, with average molecular weights from 200 to 6000. Also suitable are polyoxyethylene alcohols and esters; many of the polyoxyethylene ethers, alcohols and esters are sold under the trade name Brij, i.e., Brij 30, 52, 56, 58, 72, 76, 700, 721, 92, 93, 96, 97, 98, 99, etc. Any of these compounds can be used in the compositions of the present invention. Preferred are polyoxyethylene ethers; most preferred is polyoxyethylene 9-lauryl ether.

The above-described components of the present composition are contained in a suitable solvent. The term "suitable solvent" is used herein to refer to any solvent in which the components of the present invention can be solubilized, in which compatibility problems do not arise, and which can be administered to a patient. Any suitable aqueous or nonaqueous solvent can be used. A particular preferred solvent is water. Other suitable solvents include alcohol solutions, especially ethanol. Alcohol should be used at concentrations that will avoid precipitation of the components of the present compositions. It has been found that with the use of morphine as the pharmaceutical agent, in particular, a combination of water and ethanol is required if the composition is to be aerosolized with a propellant. The use of ethanol in combination with water provides additional solubility of the micellar formulation in the propellant. Enough of the solvent or combination of solvents should be added so that the total of all of the components in the composition is 100 wt./wt. %, i.e., solvent to q.s. Typically, some portion of the solvent or solvents will be used initially to solubilize the pharmaceutical agent prior to the addition of the micelle-forming compounds.

The present compositions optionally contain a stabilizer and/or a preservative. Phenolic compounds are particularly suited for this purpose as they not only stabilize the composition, but they also protect against bacterial growth and help absorption of the composition. A phenolic compound will be understood as referring to a compound having one or more hydroxy groups attached directly to a benzene ring. Preferred phenolic compounds according to the present invention include phenol and methyl phenol (also known as m-cresol), and mixtures thereof.

The compositions of the present invention can further comprise one or more of the following: inorganic salts; antioxidants; and protease inhibitors. The amount of any of these optional ingredients to use in the present compositions can be determined by one skilled in the art. It will be understood by those skilled in the art that colorants, flavoring agents and non-therapeutic amounts of other compounds may also be included in the formulation. Typical flavoring agents are menthol, sorbitol and fruit flavors.

For example, some compositions, including those which contain morphine, may also contain at least one inorganic salt. Non-limiting examples of inorganic salts are sodium, potassium, calcium and zinc salts, especially sodium chloride, potassium chloride, calcium chloride, zinc chloride and sodium bicarbonate.

It will be recognized by those skilled in the art that for many pharmaceutical compositions it is usual to add at least one antioxidant to prevent degradation and oxidation of the pharmaceutically active ingredients. The antioxidant can be selected from the group consisting of tocopherol, deteroxime mesylate, methyl paraben, ethyl paraben, ascorbic acid and mixtures thereof, as well as other antioxidants known in the pharmaceutical arts. A preferred antioxidant is tocopherol. The parabens will also provide preservation to the composition.

Protease inhibitors serve to inhibit degradation of the pharmaceutical agent by the action of proteolytic enzymes. When used, protease inhibitors are preferably in a concentration of between about 0.1 and 3 wt./wt. % of the composition. Any material that can inhibit proteolytic activity can be used, absent compatibility problems. Examples include but are not limited to bacitracin and bacitracin derivatives such as bacitracin methylene disalicylates, soybean trypsin, and aprotinin. Bacitracin and its derivatives are preferably used in a concentration of between 1.5 and 2 wt./wt. % of the total composition, while soyabean trypsin and aprotinin are preferably used in a concentration of between about 1 and 2 wt./wt. % of the total composition.

The pH of the present pharmaceutical composition should typically be in the range of 5 to 8, more preferably 6 to 7. Hydrochloric acid or sodium hydroxide can be utilized to adjust the pH of the composition as needed.

The compositions of the present invention may be stored at room temperature or at cold temperature. Storage of drugs is preferable at a cold temperature to prevent degradation of the drugs and to extend their shelf life.

The present invention, therefore, provides a pharmaceutical composition in which a narcotic analgesic is encapsulated in mixed micelles formed by a combination of micelle-forming agents. The composition can be delivered through the buccal mucosa. The oral membranes offer delivery advantages, in that drugs administered through these membranes are rapidly absorbed and provide a rapid onset of action and therapeutic plasma levels, all while avoiding the first pass effect of hepatic metabolism and exposure of the drug to the hostile GI environment. An additional advantage is the easy access to membrane sites, so that the drug can be applied, localized and removed easily.

The sublingual mucosa includes the membrane of the ventral surface of the tongue and the floor of the mouth, and the buccal mucosa is the lining of the cheeks. The sublingual and buccal mucosae are relatively permeable, allowing for the rapid absorption and acceptable bioavailability of many drugs. Further, the buccal and sublingual mucosae are convenient, non-invasive and easily accessible. In comparison to the GI tract and other organs, the buccal environment has lower enzymatic activity and a neutral pH that allows for a longer effective life of the drug in vivo. The sublingual mucosa and buccal mucosa are collectively referred to herein as the "oral mucosae".

It is believed that improvements in penetration and absorption of the present mixed micellar formulations can be achieved by administering the present compositions with a pharmaceutically acceptable propellant such as tetrafluoroethane, heptafluoroethane, dimethylfluoropropane, tetrafluoropropane, butane, isobutane, dimethyl ether and other non-CFC and CFC propellants. Preferably, the ratio of pharmaceutical agent to propellant is from 5:95 to 25:75. The preferred propellant is HFA-134a (1,1,1,2-tetrafluoroethane), although any pharmaceutically acceptable propellant can be used in compositions of the present invention. When the micellar composition is combined with propellant in a metered dose dispenser, the propellant will constitute between about 5 to 95% of the total formulation, more preferably 50–90% of the total.

Preferably, the present compositions are delivered through metered dose dispensers or spray devices. Metered dose dispensers are known and are a popular pulmonary drug delivery form for some drugs. One benefit of using a metered dose device is the ability to deliver a precise amount of medication with each application, and another is that the potential for contamination is minimized because the devices are self-contained.

The present invention also provides a process for making the pharmaceutical composition of the present invention. The present compositions may be prepared by mixing a solution of the macromolecular pharmaceutical agent, the alkali metal alkyl sulfate, the isotonic agent, polyoxyethylene ethers, bile acids or salts, and optionally the stabilizer and other additives. The pharmaceutical agent should be added in an amount effective for the desired purpose. The micelle-forming compounds may be added concurrently or sequentially. Mixed micelles will form with substantially any kind of mixing of the ingredients but vigorous mixing is preferred in order to provide micelles of about 10 nanometers or less in size. The pharmaceutical agents, solvents, alkali metal alkyl sulfate, polyoxyethylene ethers, bile acids/salts and optional additives as described above for the present compositions are all suitable for use in the present processes.

In one method a first micellar composition is prepared by mixing a solution comprising the narcotic analgesic with at least the alkali metal alkyl sulfate to form the first micellar composition. The first micellar composition is then mixed with polyoxyethylene ether and bile salt to form a mixed micellar composition. In another method, a first micellar composition is prepared by mixing a solution containing the narcotic analgesic, the alkali metal alkyl sulfate and the polyoxyethylene ether; to the composition is then added a bile acid or salt, with vigorous mixing. The isotonic agent can be added at any time.

The stabilizer, preferably phenol and/or m-cresol, may be added to the mixed micellar composition to stabilize the formulation and protect against bacterial growth. Alternatively, the stabilizer may be added at the same time as any of the micelle-forming ingredients. Similarly, any of the other optional additives as described above can be added at this time. The order of adding the ingredients, including the alkali metal akyl sulfate, polyoxyethylene ethers and bile acids and isotonic agent, is not critical; they can be combined all at once, if desired.

The formulation can then be put into an aerosol dispenser and the dispenser charged with propellant, if administration by this route is desired. The propellant, which is under pressure, is in liquid form in the dispenser. When the composition of the present invention is in a dispenser, the aqueous phase may be separated from the propellant phase. Preferably, however, the ratios of the ingredients are adjusted by simple experimentation so that the aqueous and propellant phases become one, i.e., there is one phase. If there are two phases, it may be necessary to shake the dispenser prior to dispensing a portion of the contents, such as through a metered valve. The dispensed dose of narcotic analgesic is propelled from the metered valve in a fine spray.

In the case of morphine, which is intended for administration through the buccal mucosa of the mouth, a solution is made by adding water and ethanol, and adding morphine sulfate powder and stirring until the powder is dissolved and a clear solution is obtained. An alkali metal alkyl sulfate and polyoxyethylene ether may be added to the solution with low speed stirring. A typical concentration of sodium lauryl sulfate, as the alkali metal alkyl sulfate, in the aqueous solution is less than about 5 wt./wt. % of the solution. Typically, morphine is present in the micellar solution in an amount which will give a concentration of about 0.1 to 20 wt./wt. % of the final composition.

The solution so formed may then be mixed vigorously, such as by sonication or high speed stirring, to form a micelle solution. A bile salt may be added, as well as an isotonic agent. The mixing may be done with a high-speed mixer or sonicator to ensure uniform micelle particle size distribution within the composition.

In a preferred embodiment, after forming the present micellar pharmaceutical compositions, the phenol and/or m-cresol is added. As indicated above, other ingredients, such as flavoring agents, anti-oxidants, salts, protease inhibitors or other pharmaceutically acceptable compounds may also be added to an aerosol dispenser. The formulation can be placed in an aerosol dispenser, and the dispenser charged with propellant in a known manner.

The present invention also provides a metered dose aerosol dispenser with the composition of the present invention and a propellant contained therein, in which a solution containing the narcotic analgesic and the propellant are in a single phase. Suitable propellants are as described above.

The present invention also provides a method for administering the pharmaceutical compositions of the present invention, by spraying the intermixed composition into the mouth with a metered dose spray device. Application can be to the buccal cavity by spraying into the cavity, while resisting inhalation. It may be necessary or desirable to shake the dispenser prior to spraying the present pharmaceutical composition and propellant into the buccal cavity. The plasma levels and blood morphine levels when orally administering the present morphine-containing compositions are comparable to those achieved when morphine is injected; the present methods offer significant improvements in the quality of life over injection, including needle-free therapy and improved convenience.

The specific concentrations of the above ingredients can be determined by one skilled in the art based upon the general guidelines provided herein. It will be understood that the amounts of certain ingredients may need to be limited in order to avoid compositions which produce foam when sprayed rather than forming a fine spray. For absorption through the oral cavities, it is often desirable to increase, such as by doubling or tripling, the dosage of pharmaceutical agent which is normally required through injection or administration through the gastrointestinal tract.

The desired size of aerosol droplets which are sprayed from the aerosol dispenser will depend, in part, on where the pharmaceutical is to be deposited. For example, for deposition in the lungs, particle sizes of less than about 5 μm are preferred whereas for absorption in the buccal cavity of the mouth, particle sizes of about 5–10 μm are preferred.

Administration of the formulation into the buccal cavity, according to any of the present methods, is by spraying the formulation into the mouth, while resisting inhalation, so that the droplets stay in the mouth rather than being drawn into the lungs.

EXAMPLES

The following example is intended to illustrate the invention, and should not be considered as limiting the invention in any way.

The following formulation was administered to the buccal mucosa of healthy subjects:

Quantity of Excipients in a 100 ml batch:

| | |
|---|---|
| Morphine Sulfate | 10 g |
| Polyoxyethylene-9-Lauryl Ether | 4.5 g |
| Glycerin | 6.0 g |
| Phenol | 5.0 g |
| Sodium Lauryl Sulfate | 4.0 g |
| Sodium Glycocholate | 3.0 g |
| Ethanol | 20 ml |
| Water for Injection | q.s. 100 ml |

These ingredients were combined and mixed vigorously with high speed stirring. One milliliter of formulation was then charged to a 10 ml metered dose dispenser, along with a propellant (1,1,1,2-tetrafluoroethane). The aerosol formulation was administered to the buccal mucosa of the subject by spraying, while resisting inhalation. Plasma levels of the drug were then measured. The results are shown in Table 1, and also graphically displayed in FIG. 1. Comparisons are made with tablet and injectable forms of the drug.

TABLE 1

Avg of 16 healthy subjects

Avg Data

| Time (mins) | INJ 5 mg | BUCCAL 5 mg | TAB 10 mg | BUCCAL 3 mg | INJ 3 mg |
| --- | --- | --- | --- | --- | --- |
| 0 | 2.58 | 3.54 | 0.3 | 0.86 | 0.26 |
| 10 | 51.87 | 17.47 | 0.21 | 5.2 | 34.16 |
| 20 | 53.68 | 29.86 | 11.87 | 6.76 | 28.07 |
| 30 | 37.53 | 43.62 | 17.07 | 11.53 | 23.91 |
| 40 | 38.13 | 58.39 | 16.72 | 15.56 | 24.71 |
| 50 | 46 | 59.7 | 15.52 | 16.16 | 21.39 |
| 60 | 44.07 | 53.83 | 11.72 | 16.06 | 14.43 |
| 75 | 23.8 | 47.07 | 13.33 | 19.72 | 13.21 |
| 90 | 23.58 | 35.48 | 10.04 | 15.33 | 11.82 |
| 120 | 25.88 | 32.29 | 8.32 | 17.09 | 12.11 |
| 150 | 23.53 | 44.92 | 7.4 | 10.79 | 9.18 |
| 180 | 18.15 | 35.43 | 4.19 | 9.72 | 5.07 |
| 210 | 13.97 | 26.7 | 2.17 | 8.72 | 5.95 |
| 240 | 7.92 | 20.74 | 1.75 | 6.79 | 3.84 |
| 300 | 4.96 | 16.6 | 1.44 | 5 | 3.39 |

Whereas particular embodiments of this invention have been described above for purposes of illustration, it will be evident to those skilled in the art that numerous variations of the details of the present invention may be made without departing from the invention as defined in the appended claims.

What is claimed is:

1. A pharmaceutical composition for pain relief comprising:
   an effective amount of a narcotic analgesic in micellar form, an alkali metal alkyl sulfate, a polyoxyethylene ether or pharmaceutically acceptable salts thereof, and a suitable solvent;
   said alkali metal alkyl sulfate and polyoxyethylene ether each present in a concentration of between about 0.1 and 30 wt./wt. % of the total composition;
   and the total concentration of the alkali metal alkyl sulfate and polyoxyethylene ether together is less than about 50 wt./wt. % of the total composition.

2. The composition of claim 1, wherein the alkali metal alkyl sulfate is present in a concentration of less than about 5 wt./wt. % of the total composition.

3. A composition according to claim 1, wherein the alkali metal alkyl sulfate is an alkali metal C8 to C22 alkyl sulfate.

4. A composition according to claim 3, wherein the alkali metal C8 to C22 alkyl sulfate is sodium lauryl sulfate.

5. A composition according to claim 1, further comprising an isotonic agent, present in a concentration of about 0.1 to 30 wt./wt. % of the total formulation.

6. The composition of claim 5, wherein said isotonic agent is glycerin.

7. A composition according to claim 1, wherein said polyoxyethylene ether is present in a concentration of between about 0.1 and 5 wt./wt. % of the total composition.

8. The composition of claim 7, wherein said polyoxyethylene ether is polyoxyethylene 9-lauryl ether.

9. The composition of claim 1, further comprising a bile acid or bile salt, present in a concentration of about 0.1 to 30 wt./wt. % of the total formulation.

10. The composition of claim 9, wherein said bile salt is sodium glycholate.

11. The composition of claim 1, wherein the narcotic analgesic is morphine.

12. The composition of claim 1, wherein the pH of said composition is between about 5 and 8.

13. The composition of claim 1, wherein the size of said micelles is between about 1 and 10 nanometers.

14. The composition of claim 1, wherein said solvent comprises a combination of water and ethanol.

15. The composition of claim 1, further comprising one or more of the members selected from the group comprising a phenolic compound, an antioxidant, a protease inhibitor, and an inorganic salt.

16. The composition of claim 15 wherein said composition comprises a phenolic compound selected from the group phenol, m-cresol and mixtures thereof, in a concentration of between about 0.1 and 10 wt./wt. % of the total composition.

17. The composition of claim 15 wherein the antioxidant is selected from the group tocopherol, deteroxime mesylate, methyl paraben, ethyl paraben, ascorbic acid and mixtures thereof.

18. The composition of claim 15 wherein the protease inhibitor is selected from the group bacitracin, bacitracin methylene disalicylates, soybean trypsin and aprotinin.

19. The composition of claim 15 wherein the inorganic salt is selected from the group sodium, potassium, calcium and zinc salts.

20. The composition of claim 1, further comprising a propellant, present in a concentration of about 50–95% of the total formulation.

21. The composition of claim 19, wherein said propellant is selected from the group consisting of tetrafluoroethane, heptafluoroethane, dimethylfluoropropane, tetrafluoropropane, butane, isobutane and dimethyl ether.

22. A process for making a pharmaceutical composition comprising:
   mixing an effective amount of a narcotic analgesic in a suitable solvent with an alkali metal alkyl sulfate and a polyoxyethylene ether or pharmaceutically acceptable salts thereof, to form a mixed micelle pharmaceutical composition;
   the alkali metal alkyl sulfate and polyoxyethylene ether each present in a concentration of between about 0.1 and 30 wt./wt. % of the total composition;
   and the total concentration of the alkali metal alkyl sulfate and polyoxyethylene ether together is less than 50 wt./wt. % of the total composition.

23. The process of claim 22, further comprising the step of adding a bile acid or bile salt.

24. The process of claim 22, further comprising the step of adding an isotonic agent.

25. The process of claim 22, further comprising the step of adding a stabilizer.

26. The process of claim 22, further comprising the step of adding one or more compounds selected from the group consisting of a preservative, an antioxidant, a protease inhibitor and an inorganic salt.

27. The process of claim 22, wherein said mixing is effected by use of a high speed stirrer selected from the group magnetic stirrers, propeller stirrers, and sonicators.

28. A method for treating a patient for pain relief comprising administering to said patient an effective amount of the pharmaceutical composition of claim 1.

29. The method of claim 28, wherein said administration is oral.

30. The method of claim 28, wherein said administration is buccal.

31. A method for enhancing the rate of absorption of a narcotic analgesic in a patient comprising administering a composition comprising said narcotic analgesic in conjunction with an alkali metal alkyl sulfate and a polyoxyethylene ether or pharmaceutically acceptable salts thereof;

the alkali metal alkyl sulfate and polyoxyethylene ether each present in a concentration of between about 0.1 and 30 wt./wt. % of the total composition;

and the total concentration of the alkali metal alkyl sulfate and polyoxyethylene ether together is less than 50 wt./wt. % of the total composition.

32. The composition of claim 1, wherein the narcotic analgesic is fentanyl.

* * * * *